(12) United States Patent
Wild et al.

(10) Patent No.: US 7,278,292 B2
(45) Date of Patent: Oct. 9, 2007

(54) METHOD OF ASSESSING THE PRODUCT SHELF LIFE IN A PACKAGE

(75) Inventors: Hans-Peter Wild, Eppelheim/Heidelberg (DE); Klaus Küssner, Gaiberg (DE); Frank Spinner, Karlsruhe (DE)

(73) Assignee: Rudolf Wild GmbH & Co. KG, Eppelheim (DE)

( * ) Notice: Subject to any disclaimer, the term of this patent is extended or adjusted under 35 U.S.C. 154(b) by 0 days.

(21) Appl. No.: 11/184,496

(22) Filed: Jul. 19, 2005

(65) Prior Publication Data
US 2006/0032293 A1  Feb. 16, 2006

(30) Foreign Application Priority Data
Aug. 12, 2004  (DE) .................. 10 2004 039 210

(51) Int. Cl.
*G01N 15/08* (2006.01)
*G01N 17/00* (2006.01)

(52) U.S. Cl. ................... 73/38; 73/40.7; 73/52
(58) Field of Classification Search ............... 73/38, 73/40, 40.5 R, 40.7, 52
See application file for complete search history.

(56) References Cited

U.S. PATENT DOCUMENTS

| | | | | |
|---|---|---|---|---|
| 4,047,422 | A * | 9/1977 | Lyssy .............................. | 73/38 |
| 5,029,464 | A * | 7/1991 | Lehmann .................... | 73/49.3 |
| 5,254,354 | A * | 10/1993 | Stewart ....................... | 426/106 |
| 5,361,625 | A * | 11/1994 | Ylvisaker ....................... | 73/38 |
| 6,640,615 | B1 * | 11/2003 | Morrow ......................... | 73/38 |
| 6,834,532 | B2 * | 12/2004 | Izutsu et al. ................... | 73/38 |
| 6,892,567 | B1 * | 5/2005 | Morrow ......................... | 73/38 |

(Continued)

FOREIGN PATENT DOCUMENTS

WO  WO9210414 A1 * 6/1992

OTHER PUBLICATIONS

Norenberg et al., "Pressure-Dependent Permeation of Noble Gases Through Thin Membranes of Oriented Polypropylene (OPP) Studied by Mass Spectrometry", Polymer 42, 2001, pp. 10021-10026.*

*Primary Examiner*—Hezron Williams
*Assistant Examiner*—David A. Rogers
(74) *Attorney, Agent, or Firm*—Stroock & Stroock & Lavan LLP

(57) ABSTRACT

A method for the assessment of the product shelf life in a package, and a device for accelerating the permeation of a test gas into a package. To significantly reduce the test time and to accelerate the permeation of a test gas, and in order to supply realistic results of the time-dependent permeations into the charged product in a simple manner, a closed package filled with charged product is placed in an overpressure chamber, and stored in the overpressure chamber over a specified time period under overpressure and at a specified temperature in a test gas atmosphere, wherein a defined amount of test gas permeates into the package. The package is stored over a certain time period under the influence of heat and/or light and then the charged product is subjected to analytical and/or sensory examination. The device includes an overpressure container for the accommodation of at least one package with a closable inlet opening, a gas inlet for feeding the test gas, a gas outlet for discharging the test gas, and a device for setting and maintaining an overpressure.

20 Claims, 2 Drawing Sheets

U.S. PATENT DOCUMENTS 6,964,191 B1 * 11/2005 Tata ............................... 73/38
2002/0194899 A1 * 12/2002 Gebele et al. .................. 73/38
2004/0040372 A1 * 3/2004 Plester et al. .................. 73/38
2004/0177676 A1 * 9/2004 Moore ........................... 73/38

* cited by examiner

METHOD OF ASSESSING THE PRODUCT SHELF LIFE IN A PACKAGE

REFERENCE TO RELATED APPLICATION

This disclosure claims priority to German Application No. 102004039210-2, filed Aug. 12, 2004.

FIELD OF THE DISCLOSURE

The disclosure relates to a method of assessing the product shelf life in a package, as well as to a device for accelerating the permeation of a test gas into a package.

BACKGROUND OF THE DISCLOSURE

In particular in the foodstuffs sector the various packages must ensure optimum protection for the product. Both with regard to the material selection and the design of the package, the package must here fulfil high requirements specific to the product charged. Perfect product quality must be guaranteed within the declared minimum shelf life. Apart from the microbiological preservability, which can be ensured by suitable methods, such as heating, aseptic filling and packing, as well as preservation, essentially the chemical or physical changes of the charged product, which can lead to aromatic changes, are also of essential concern. In particular, the permeation of substances, particularly such as oxygen, through the package and the subsequent modification of the composition of the charged product by these substances can influence the quality of the product in decisive ways.

Apart from material inspection tests and theoretical computational models, standard qualification tests, such as a product storage test in real time are available for the determination of the minimum shelf life. Here, the package to be investigated is filled and stored over the time period of the intended minimum shelf life under controlled conditions. This means however that an adequately reliable conclusion about the suitability of a package design for an existing product or, vice versa, a new product development for an existing type of package can only be made after the intended minimum shelf life has expired. The main disadvantage of this test method lies in this very long testing period of several months. Due to the increasingly larger variety of products, increasingly shorter product life cycles with at the same time a high expectancy on the part of the consumer with regard to product quality and reliability, within the competition amongst product suppliers there is the necessity of reducing the required development time.

SUMMARY OF THE DISCLOSURE

On the basis of this, the object of the disclosure is to provide a method of assessing the product shelf life in a package and a device for accelerating the permeation of a test gas into a package, which substantially reduce the testing time and supply realistic results of the time-dependent permeation in the charged product inResponse to Missing Parts and Assignment for recordation with U.S. Patent Office. a simple way.

According to this disclosure, the process of permeation of test gas into the package can be accelerated in time by increasing the pressure $p_1$. In this case the degree of permeation depends linearly on the real permeability of the package under ambient pressure (standard pressure) in real time. Through the following storage of the package over a certain time period under heat and/or the influence of light, the interaction of the gas content, present to a larger extent due to forcing, with other substances contained in the products can occur. Consequently, a realistic impression of storage over several months arises. Aromatic changes, which occur due to the combined effect of light and oxygen, can be simulated by additional exposure to light. The method according to the disclosure facilitates a rapid assessment method, which can be carried out in one or a few weeks and therefore in comparison to real-time tests, which take several months, results in a clear time saving. Consequently, the compatibility of an existing product with a certain package can be determined in a simple manner in a short time with regard to the optimum product quality.

According to a preferred embodiment of this invention the test gas comprises $O_2$ or is composed of pure $O_2$. Thus, the time-dependent intake of oxygen by the charged product due to the gas permeability of the package can be simulated in the course of the storage period.

Preferably, the temperature $T_1$ in step b) lies in a range from 5 to 40° C., preferably at room temperature in a range from 15 to 25° C. The overpressure $p_1$ is preferably in a range from 0.1 to 2.5 MPa.

Since the permeation also depends on the relative moisture content in the overpressure chamber, it is advantageous to also adjust the relative moisture content in the overpressure chamber, preferably in a range from 40 to 50%. Thus, comparable test parameters are present during the various measurements.

In step c) the temperature $T_2$ at which the package is stored over a certain time period under heat, lies in a range from 25 to 60° C. Thus, interactions of the test gas content, present to a larger extent due to forcing, with other content substances of the products are accelerated and amplified.

According to this disclosure, additionally a real storage time period $t_{real}$ equivalent to the time period $t_1$ can be determined in which at standard pressure the same defined amount Q of test gas permeates into the package. Thus, it is possible in a short time, i.e. in a few days, to draw a conclusion about the product shelf-life time period: Alternatively to this, the time $t_1$ and the overpressure $p_1$ and the temperature $T_1$ can also be defined for step b) such that a defined amount Q of test gas permeates into the package, corresponding to the amount $Q_{real}$, which permeates into the package under ambient pressure (standard pressure) in real time. With this type of implementation, it is possible, for example, to establish in a short time whether a package is suitable for a certain product.

This method is particularly suitable for plastic bottles.

In step c) the time period $t_2$ lies preferably in a range from 48 to 720 hours.

According to a preferred embodiment, after step c) with a carbonated charged product, the $CO_2$ content of the charged product is adjusted such that it corresponds to the $CO_2$ content which the charged product would have after storage in real time $t_{real}$ in order to set the $CO_2$ loss realistically for the sensory assessment.

The device according to the disclosure for accelerating the permeation of a test gas into a package is simply constructed and can be realized inexpensively. Preferably, the device exhibits a heating device in order to maintain the at least one package at a certain temperature $T_1$ to ensure reproducible test conditions. Furthermore, the device can exhibit a facility for selling the relative moisture content in the overpressure container to obtain reproducible permeation conditions. The pressure container can be operated in an overpressure range from 0.1 to 2.5 MPa, preferably up to 1 MPa.

According to a preferred embodiment of this disclosure, the gas outlet is connected to a gas measurement system for the analysis of the atmospheric composition of the test gas inside the overpressure container.

BRIEF DESCRIPTION OF THE DRAWINGS

This disclosure is explained in more detail in the following with reference to the enclosed drawings.

DETAILED DESCRIPTION OF THE DISCLOSURE

Figure 1:
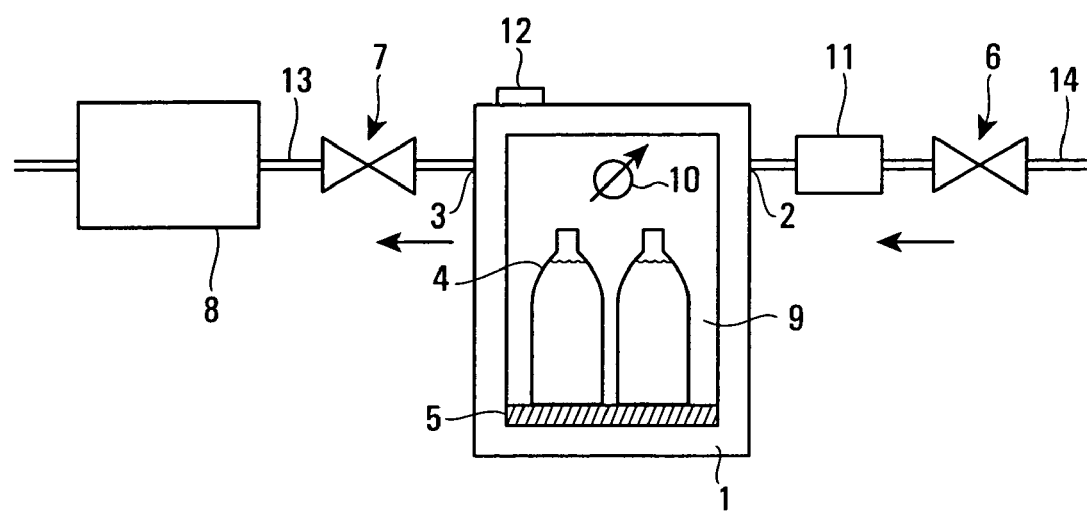
FIG. 1 shows a schematic diagram of a device according to the disclosure.

As can be seen from FIG. 1, the device according to the disclosure comprises an overpressure container 1 for the accommodation of at least one filled and closed package; here, for example, two PET bottles 4 arranged adjacently. The overpressure container 1 exhibits a closable inlet opening 9. The overpressure container 1 can be operated in an overpressure range from 0.1 to 2.5 MPa and furthermore exhibits an overpressure safety device 12, which reduces the overpressure via a valve (not shown) at a pressure which is above the operating pressure. Furthermore, the device according to the disclosure exhibits a gas inlet 2 for feeding a test gas and a gas outlet 3 for discharging the test gas. A feed line 14 is connected to the gas inlet 2 and a discharge line 13 is connected to the gas outlet 3. The feed line 14 comprises an inlet valve 6 and the discharge line 13 comprises an outlet valve 7. The device, in addition, comprises a facility for setting and maintaining an overpressure $p_1$. The device also comprises a gas pressure gauge 10 for the measurement of the pressure $p_1$ in the overpressure chamber 1. The gas pressure gauge 10 can here, as illustrated in FIG. 1, be arranged in the overpressure chamber, but it is also possible to provide the gas pressure gauge in the feed or discharge line 13, 14 in the region of the gas inlet or outlet 2, 3. Thus for example, with the inlet valve 6 open test gas can be fed to the overpressure chamber 1 via the feed line 14 until the gas pressure gauge 10 indicates a certain overpressure $P_1$. The device can also exhibit an electronic controller, which is not shown, and which controls the gas pressure in the overpressure chamber 1.

The device preferably exhibits a heating device 5 which enables the packages 4 to be maintained at a predetermined temperature $T_1$ to achieve reproducible test conditions.

Furthermore, the device according to the disclosure comprises a facility 11 for adjusting the relative humidity. Since the relative humidity is a criterion for the permeation of test gas into the package 4, it is advantageous if a certain relative humidity can be set in the overpressure chamber. As a device for setting the relative humidity, for example, a pipe intermediate piece filled with plastic fleece and safe against overpressure can be used which can be soaked with, for example, distilled water via a separate connecting piece. The quantity of water, for example calculated with the aid of a Mollier h-X graph and the value of the pressure to be obtained in the container which is needed for setting a defined relative humidity in the container atmosphere, can thus be applied to the plastic fleece. During the filling of the container with gas, the gas flows through the fleece, evaporates the water and carries the water vapour into the container with it.

With this embodiment the gas outlet 3 or the discharge line 13 is connected to a gas measurement system 8, which analyses the atmospheric composition inside the overpressure chamber 1. The gas measurement system is based for example on electrochemical sensor technology and can measure a number of gases simultaneously (e.g. qualitatively and quantitatively) (e.g. Dräger multi-gas scanner).

The feed line 14 is connected to a gas panel which is not shown in order to feed in a test gas or a certain test gas mixture.

With the device according to the disclosure the permeation of a test gas into the package 4, here the PET bottles 4, can be accelerated. During the permeation into the package 4, gases and vapors are deposited on the surface of the permeable package, they diffuse through the package due to the concentration gradient and pass into the charged product. During the permeation the permeate is initially dissolved in the plastic until an equilibrium concentration occurs (lag phase). Then the actual permeation of the test gas takes place linearly according to the following equation (1):

$$Q/t = P/X \, A \, \Delta p.$$

Here, Q is the total amount of permeate, which passes through a plastic layer of area A and thickness X in the time t; $\Delta p$ is the partial pressure difference of the permeate between the outer and inner sides of the plastic and P is a permeability coefficient which is specific to the substance for the package material and the permeate. Thus the total amount of permeate Q is linearly dependent on the difference of the test gas partial pressure outside and inside the package. The concentration or the partial pressure of the test gas, e.g. $O_2$ within the package is neglected, so that the partial pressure difference is equal to the absolute pressure of the test gas, i.e. here the oxygen, outside the package. In a standard atmosphere (T=1013 mbar) the partial pressure of oxygen P ($O_2$)=0.21222235 bar. Thus, by increasing the partial pressure it is possible to obtain the same amount of permeating test gas, here oxygen, in a shorter time. This linear relationship applies at constant temperature. If, for example, the partial pressure is increased for an ideal test gas (e.g. 100% of oxygen) by the factor 38.6, so that $\Delta p$=8.1 bar, then the real storage time period $t_{real}$ can be reduced from for example 9 months to 7 days.

The degree of forced permeation is here linearly dependent on the real permeability of the package.

Figure 2:
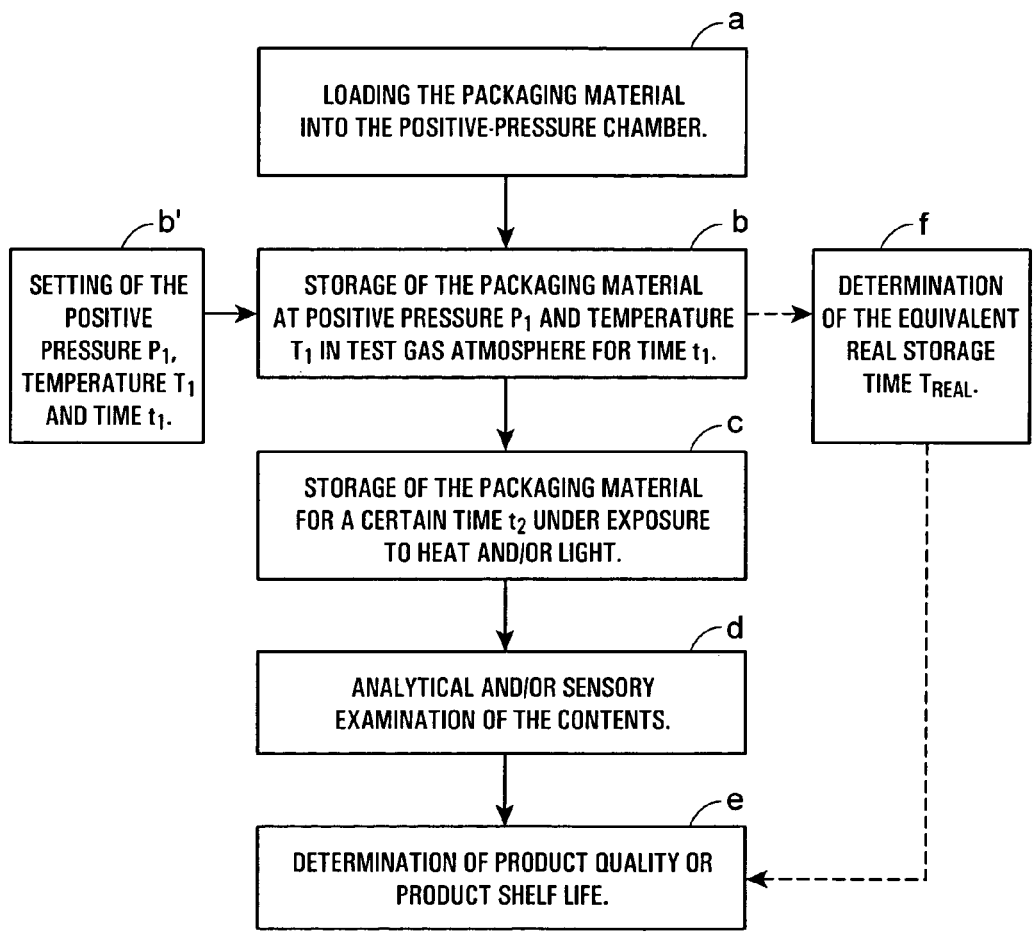
FIG. 2 schematically shows a flow chart of an embodiment of the method according to the disclosure.

In the following the method according to the invention is explained in more detail with reference to FIG. 2.

Firstly, the filled and closed packages 4, here the PET bottles 4, are placed in the overpressure chamber 1 and the inlet opening 9 closed pressure tight (step a). Before storing the package in the overpressure chamber 1, the corresponding test parameters were determined, wherein the level of the overpressure $p_1$, the temperature $T_1$ and the time $t_1$ for storing the package 4 in the test gas atmosphere were defined (step b')). In the overpressure chamber 1 the determined overpressure $P_1$ is then set by the facility for setting and maintaining the overpressure $p_1$. Furthermore, a certain temperature $T_1$ is set via the heating device 5, as well as a certain relative humidity via the facility for setting the relative humidity 11. The temperature, the overpressure and the relative humidity are held constant for the total test duration $t_1$. The storage under overpressure $p_1$ accelerates, the permeation process through the package as previously explained. Here, the temperature $T_1$ is preferably in a range from 15 to 25° C., the overpressure $p_1$ in a range from 0.1 to 2.5 MPa, the time $t_1$ in a range from 0-240 hours and the relative humidity in a range from 0 to 100%.

After the time period $t_1$ the pressure in the overpressure chamber 1 is reduced to the ambient pressure and the package 4 removed from the overpressure chamber 1.

In step c) the package 4 is now stored over a specified time period $t_2$, which for example can be 48 to 720 hours, under the influence of heat and/or light. The step c) is necessary so that interactions of the test gas content, largely present due to forcing, with other substances contained in the products are accelerated and amplified.

With storage in the dark in a temperature range from 25 to 60° C. at ambient pressure over a time period from 48 to 720 hours in the case of oxygen as the test gas, reactions due to oxygen can occur which correspond to the reactions due to oxygen under normal storage conditions (storage over a real storage time period $t_{real}$ equivalent to several months at ambient pressure and ambient temperature). Thus, a realistic simulation of several months of storage can be produced.

At the same time or alternatively to this, the packages 4 can be subjected to a separate light treatment in step c) to permit aromatic changes to take place which arise due to the combined effect of light and test gas, here oxygen. In this case the packages are subjected to a constant light intensity of 50 to 750 W/m² over a time period of 1 to 10 hours. This can, for example, occur using a standardised test device, preferably Suntest XLS+from Atlas Material Testing Technology, or also by irradiation of the samples with neon light at a short distance.

Following step c) the analytical and/or sensory assessment of the charged product can now take place. During the analytical and/or sensory assessment of the charged product, the charged product is compared with a comparative sample which has been filled into an impermeable package and stored cool (T=1 to 10° C.) and in the dark until the testing time.

During the sensory assessment of the charged product, the samples are assessed, for example in a "Difference from Control Test", against the previously mentioned standard, i.e. the comparative sample is tasted and the deviation from the standard is assessed.

The product changes during the test method can also be analytically assessed, wherein for example the content of L-ascorbic acid or the content of aromatic substances relevant to the charged product is quantified for example by HPLC or GC methods and compared with the previously mentioned standard. Similarly, aroma profiling is also possible, wherein an aroma profile of a reference sample, with which the charged product has as previously described been filled and stored cool and dark in an impermeable package, is produced and compared with the aroma profile of the charged product which has been treated according to this method.

Then, from the analytical and/or sensory examination of the charged product, a statement about the product quality can be made which enables a conclusion to be drawn about the minimum shelf life.

With the method according to the invention the minimum shelf life can be determined in that starting with the time period $t_1$, a real storage time $t_{real}$ (step f) equivalent to the time period $t_1$ is calculated in which at ambient pressure (standard pressure) the same defined quantity Q of test gas would permeate into the package, at which the assessed product quality is still adequate.

Alternatively to this, in step b') the individual parameters, such as overpressure $p_1$, temperature $T_1$ and time $t_1$, can already be calculated such that the quantity Q of test gas which permeates into the package 4 corresponds to the quantity Q which would permeate into the package in the real-time test during the real storage time $t_{real}$ at ambient pressure and at the appropriate temperature. In step e) the product quality can then be determined (in relation to the analytical and sensory examinations of the charged product carried out in step d)), so that for example a statement can be made of whether a certain package is suitable for an existing product with a certain product shelf life or, vice versa, there is the possibility of selecting the best one for an existing package from a number of product variants. Furthermore, for example, an orientating comparison of new product developments can be made with current market samples (benchmarks).

The calculation of the appropriate parameters occurs, for example, using the equation (1).

Since with the carbonised charged product in step b) the $CO_2$ content during the time period $t_1$ reduces to a less extent than in the equivalent real storage time $t_{real}$, the $CO_2$ content $C_{target}$ between steps c) and d) is set such that it corresponds to the $CO_2$ content $C_{real}$, which the charged product would have after storage over the real-time storage period $t_{real}$. The corresponding $CO_2$ content is determined with sufficient approximation, for example, according to equation (2).

$$C_{real} = PV^{-1}A\, t_{real}$$

P=Permeability coefficient of a plastic film of specified thickness for a test gas for a temperature of T=20° C. [g m$^{-2}$bar$^{-1}$d$^{-1}$]

A=Area of bottle [m²]

V=Bottle nominal volume [l]

$t_{real}$=Real time [d]

The content of $CO_2$ in the product is proportional to the equivalent pressure at the product level. With plastic bottles the setting therefore occurs using a bottle tapping apparatus which facilitates via a valve the controlled reduction of the equivalent pressure which is read on a pressure gauge.

The balancing of the $CO_2$ content to the value to be expected from calculation only has an effect on the sensory overall impression and has no effect on any aromatic changes which are detected analytically. An accuracy of +/−0.3 g/l is therefore sufficient.

Summarizing, it can be concluded that with the method according to the disclosure and with the device according to the disclosure prolonged real-time tests for the determination of the product quality with regard to permeation processes are superfluous. Through the combined storage of the package under overpressure followed by storage of the package under heat and/or light, a realistic simulation of the permeation in the package can be realized.

The invention claimed is:

1. Method for the assessment of a product shelf life in a package, comprising the following steps of:
    a) placing a closed package (4), filled with the charged product, in an overpressure chamber (1);
    b) storing the package (4) in the overpressure chamber (1) over a time period $t_1$ at overpressure $p_1$ and at a certain temperature $T_1$ in a test gas atmosphere, wherein a defined amount Q of the test gas permeates into the package;
    c) storing the package (4) over a certain time period $t_2$ under the influence of heat and/or light; and
    d) conducting analytical and/or sensory examination of the charged product, subsequent to storing the package over time period $t_2$, for an amount of the test gas.

2. Method according to claim 1, wherein the test gas comprises $O_2$.

3. Method according to claim 2, wherein the test gas comprises pure $O_2$.

4. Method according to claim 1, wherein the temperature $T_1$ in step b) lies in a range from approximately 5° C. to 40° C.

5. Method according to claim 4, wherein the temperature $T_1$ in step b) lies in the range from approximately 15 to 25° C.

6. Method according to claim 1, wherein in step b) the overpressure $p_1$ lies in a range up to approximately 2.5 MPa.

7. Method according to claim 1, wherein in step b) in the overpressure chamber (1) a relative settable moisture content is set which lies in a range from approximately 0 to 100%.

8. The method according to claim 1, wherein the temperature $T_2$ in step c) lies in a range from approximately 25 to 60° C.

9. Method according to claim 1, and the additional step of determining a real storage time period $t_{real}$ equivalent to the time period $t_1$ in which the same defined quantity Q of the test gas permeates into the package (4) at ambient pressure (standard pressure) $P_{standard}$.

10. Method according to claim 1, wherein for step b) the time $t_1$ and the overpressure $p_1$ as well as the temperature $T_1$ are established such that a defined amount Q of test gas permeates into the package (4), which corresponds to the amount $Q_{real}$, which permeates into the package in real time at ambient pressure (standard pressure) $P_{standard}$.

11. Method according to claim 1, wherein the package is a plastic bottle.

12. Method according to claim 1, wherein in step c), the time period $t_2$ lies in a range from 48 to 720 hours.

13. Method according to claim 1, in that after step c), when in connection with carbonized $CO_2$ charged product, the step of setting the $CO_2$ content of the charged product to correspond to the $CO_2$ content which the charged product would have after storage over the real-time storage period $t_{real}$.

14. The method according to claim 1, wherein in step b) in the overpressure chamber (1) a relative moisture content is set which lies in a range from approximately 40 to 50%.

15. The method according to claim 1, comprising accelerating the permeation of the test gas into the package (4) by using a device comprising: an overpressure container (1) for the accommodation of at least one package (4) with a closable inlet opening (9), a gas inlet (2) for feeding in the test gas, a gas outlet (3) for discharging the test gas, and a facility for setting and holding an overpressure ($p_1$).

16. The method according to claim 15, wherein the device comprises a heating device (5) for maintaining the at least one package (4) at a certain temperature $T_1$.

17. The method according to claim 15, wherein the device comprises a facility (11) for setting the relative moisture content in the overpressure container (1).

18. The method according to claim 15, wherein the gas outlet (3) is connected to a gas measurement system (8) for the analysis of the atmospheric composition of the test gas inside the overpressure container.

19. The method according to claim 15, wherein the container can be operated in a pressure range up to approximately 2.5 MPa.

20. The method according to claim 19, wherein the pressure range is up to approximately 2.0 MPa.

* * * * *